United States Patent [19]

Sukman

[11] 3,989,824

[45] Nov. 2, 1976

[54] METHOD FOR CONTROLLING ACARIDS WITH PHOSPHINE OXIDES

[75] Inventor: Edwin L. Sukman, Fanwood, N.J.

[73] Assignee: M & T Chemicals Inc., Greenwich, Conn.

[22] Filed: Mar. 6, 1975

[21] Appl. No.: 555,884

[52] U.S. Cl. .................... 424/204; 424/168; 424/357
[51] Int. Cl.$^2$ .................................. A01N 9/36
[58] Field of Search ............... 424/204, 222; 260/606.5 P

[56] References Cited
UNITED STATES PATENTS

| | | | |
|---|---|---|---|
| 3,020,315 | 2/1962 | Campbell et al. | 260/606.5 P |
| 3,032,589 | 5/1962 | Hoffman et al. | 260/606.5 P |
| 3,035,096 | 5/1962 | Cooper | 260/606.5 P |

OTHER PUBLICATIONS

Hoffman et al. 1962, Chem. Abs., vol. 56, pp. 15536 to 15537.
Hellmann et al., 1962, Chem. Abs., vol. 56, p. 11616.
Kabachnik et al. Chem. Abs., 1967, vol. 58, p. 5720.
Kumada et al., Chem. Abs., 1963, vol. 59, p. 8782.
Goetz et al., Chem. Abs., 1963, vol. 59, pp. 11221 and 11222.
Seyferth et al. Chem. Abs.; 1964, vol. 61, p. 5687.
Griffin, Chem. Abs., 1965, vol. 62, pp. 3905 and 3906.
Isslieb et al., Chem. Abs., 1965, vol. 62, p. 9169.
Bacon Chem. Abs., 1966, vol. 64, pp. 8239–8240.

*Primary Examiner*—Dale R. Ore
*Attorney, Agent, or Firm*—Robert P. Auber; Kenneth G. Wheeless; Robert Spector

[57] ABSTRACT

Acarids, including spider mites, are effectively controlled by applying to the acarids, their habitat or both certain tertiary bis(halophenyl)phosphines, phosphine oxides and phosphine sulfides. These compounds kill adult and nymph acarids in addition to their eggs.

8 Claims, No Drawings

METHOD FOR CONTROLLING ACARIDS WITH PHOSPHINE OXIDES

BACKGROUND

This invention relates to the control of acarids. This invention further relates to compositions for controlling acarids, including mites, that can be applied directly to these organisms, their eggs or to areas, particularly plants, that are infested with these organisms.

Numerous phosphorus compounds have been disclosed as being effective control agents for acarids. For example, U.S. Pat. No. 2,754,242 teaches using alkyl bis(halophenyl)phosphinates to kill two-spotted spider mites. Many of these compounds are not practical for use as commercial insecticides, since they must be present at relatively high concentration levels (500 parts per million or more) to be effective. The in-use cost of these prior art materials may therefore be so high as to exclude them for large-scale applications.

It has now been found that certain tertiary bis(halophenyl)phosphines, phosphine oxides and phosphine sulfides are remarkably effective acaricides that can be employed at lower concentration levels than heretofore possible using many structurally related prior at materials, including those disclosed in the aforementined U.S. Pat. No. 2,754,242.

SUMMARY OF THE INVENTION

This invention provides a method for controlling acarids by applying to said acarids their eggs or to substrates susceptible to infestation with said acarids an acaricidally effective amount of a phosphorus compound exhibiting the formula

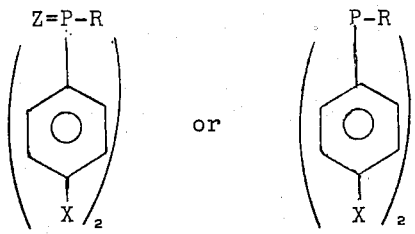

wherein R is selected from the group consistng of alkyl radicals containing between 1 and 12 carbon atoms, alkenyl and alkynyl radicals containing between 2 and 12 carbon atoms, cycloalkyl, aryl, alkaryl, aralkyl and haloalkyl radicals, X represents a halogen atom selected from the group consisting of fluorine, chlorine, bromine and iodine atoms and Z represents oxygen or sulfur.

DETAILED DESCRIPTION OF THE INVENTION

The present acaricides are tertiary bis(p-halophenyl) phosphines, phosphine oxides and phosphine sulfides. When R of the preceding formulae represents an alkyl radical, it may contain one or more halogen atoms as substituents. These compounds effectively control acarids, including spider mites, at considerably lower concentrations than can be achieved using structurally related compounds, such as the aforementioned bis(-halophenyl)phosphinates that are disclosed in the chemical and patent literature. The comparative efficacy of the present acaricides and the criticality of the substituents on both the phenyl radicals and the phosphorus atom are demonstrated in the accompanying examples. In addition to killing nymph and adult acarids, the present compounds also inhibit development of the eggs of these organisms.

While many known acaricides are effective when sprayed onto plant leaves infested with mites, the present compounds are unique in that they can also be applied to the soil surrounding the roots of the plant and are transported by the plant to the leaves, where both mites and their eggs are killed.

Many of the present tertiary bis(halophenyl)phosphines are disclosed in the chemical literature. The phosphines are conveniently prepared by reacting the appropriate halophenyl magnesium halide and dichloroorganophosphine. The dichloroorganophosphines are either available from commercial suppliers or can be synthesized using known preparative methods, for example those disclosed in "Organ-phosphorus Compounds" by G. M. Kosolapoff, published by John Wiley and Sons, Inc. The resultant bishalophenyl)organophosphine is readily converted to the corresponding phosphine oxide or phosphine sulfide by reacting the phosphine with hydrogen peroxide or elemental sulfur, respectively.

Alternatively, the phosphine oxides can be prepared directly from a halophenylmagnesium halide by reacting it with the appropriate organophosphonic dichloride,

The following examples provide specific methods for preparing representative compounds encompassed by the accompanying claims. All parts and percentages are by weight.

EXAMPLE 1

Bis(p-chlorophenyl)methylphosphine Oxide

To 900 cc. of a solution containing 1.143 moles of p-chlorophenylmagnesium bromide dissolved in tetrahydrofuran was added 73 g. (0.55 mole) of methylphosphonic dichloride

dissolved in 400 cc. of tetrahydrofuran. The addition required two hours, during which time the reaction mixture was stirred and the temperature maintained at between 30° and 40° C. Following completion of the addition the reaction mixture was heated to the boiling point for one hour, cooled and then extracted using 2 liters of chloroform. The chloroform layer was then dried using anhydrous magnesium sulfate and the solvent removed under reduced pressure. The solid residue was recrystallized once from benzene to yield 90 g. of a white solid that melted between 167° and 169° C. Analysis of the recrystallized product revealed a phosphorus content of 10.9% and a chlorine content of 22.3%. The calculated phosphorus and chlorine content of bis(p-chlorophenyl)methylphosphine oxide is 10.9 and 24.9%, respectively. The structure of the compound was confirmed by nuclear magnetic resonance.

Example 2

Bis(p-chlorophenyl)chloromethylphosphine Oxide

To a solution containing 69 g. (0.39 mole) of chloromethylphosphonic dichloride and 400 cc. tetrahydrofuran was added 285 cc. of a tetrahydrofuran solution containing 0.789 mole of p-chlorophenylmagnesium bromide. The addition was dropwise and required two hours, during which time the temperature of the reaction mixture was maintained at 30° C. Following completion of the addition the mixture was stirred for two hours while the temperature was maintained at 60° C. After the mixture had cooled to ambient temperature 400 cc. of water were gradually added, followed by 1200 cc. of methylene chloride. The organic layer was then separated, dried using anhydrous magnesium sulfate and the methylene chloride removed under reduced pressure. The residue was passed through a column of neutral alumina using ethyl acetate as the eluent. The white solid obtained following removal of the eluent and one recrystallization of the residue from benzene weighed 90 g., melted between 114° and 117° C. and exhibited the following analysis: chlorine — 32.8%; phosphorus — 9.89%. The calculated values for bis(p-chlorophenyl)chloromethylphosphine oxide are 33.3 and 9.70%, respectively. The nuclear magnetic resonance spectrum was consistent with the desired structure.

EXAMPLE 3

Bis(p-chlorophenyl)methylphosphine

To 12.6 g. of magnesium turnings was gradually added a solution containing 96 g. (0.50 mole) of p-chlorobromobenzene and 1.80 cc. tetrahydrofuran. The reaction mixture was stirred and maintained under a nitrogen atmosphere during the addition, following which the contents of the vessel were heated to reflux temperature for two hours. When the reaction mixture had cooled, a solution of methyldichlorophosphine (29.3 g., 0.25 mole) in 25 cc. tetrahydrofuran was gradually added. Following completion of this addition the reaction mixture was heated to reflux temperature for two hours. When the mixture had cooled it was slowly poured into 500 cc. of cold water and then acidified to a pH of 5 using aqueous hydrochloric acid. The resultant aqueous solution was extracted using chloroform. The organic layer was then dried over anhydrous magnesium sulfate and the chloroform removed under reduced pressure. The residue remaining followng removal of the chloroform weighed 64 g. and was distilled, the fraction boiling at between 155 and 160 under a pressure of 0.5 mm Hg being collected. This distillate converted to a white solid upon cooling. The solid material weighed 34 g. and exhibited the following analysis:

|  | Found | Calculated |
| --- | --- | --- |
| Phosphorus | 10.9% | 11.5% |
| Chlorine | 25.9% | 26.4% |

EXAMPLE 4

Bis(p-chlorophenyl)propylphosphine Sulfide

Bis(p-chlorophenyl)propylphosphine was prepared by reacting 0.2 mole of propyldichlorophosphine with a 0.4 mole of p-chlorophenylmagnesium bromide. The product was isolated by chloroform extraction and distillation as previously described. The portion boiling between 160° and 165° C. under a pressure of 2 mm. Hg was collected. The analysis corresponded to bis(p-chlorophenyl)propylphosphine.

An 18 g. (0.061 mole) portion of the phosphine was combined with 150 cc. benzene, followed by 2.1 g. (0.065 mole) of sulfur. The resultant mixture was stirred for one hour and the solvent removed under reduced pressure. Following one recrystallization from diethyl ether the solid product weighed 16 g. and melted between 102° and 107° C. This product was found to contain 9.21% phosphorus, 22.2% chlorine and 8.33% sulfur. The calculated values for bis(p-chlorophenyl) propylphosphine sulfide are 9.42, 21.6 and 9.73%, respectively.

When employed to combat acarids, particularly mites, the present phosphines, phosphine oxides and phosphine sulfides can be applied directly on the acarids, to plants infested with acarids or to plants and other substrates which are susceptible to attack by acarids. The long term residual activity and low phytotoxicity that characterize the present acaricides makes it possible to apply these compounds to plants several days, and in some instances weeks, prior to the time when the plant will be exposed to the acarids.

The present compounds are conventionally applied to plants as liquid sprays, solid dusts or wettable powder.

Compositions suitable for spraying are usually prepared by diluting liquid concentrates or wettable powders containing between 10 and 90% of the active toxicant. To avoid the expense of transporting formulations containing large amounts of inert diluents, the dilution is usually performed at the location where the spray will be applied. The concentration of toxicant in a spray to be applied to plants in a field is between 10 and 1000 parts per million (ppm), preferably between 100 and 500 parts per million.

Solid dust compositions, which are generally applied over a relatively small area, contain between 1 and 50% by weight of active toxicant, preferably between 1 and 10%.

The concentration of toxicant required in a given formulation will be dependent upon a number of parameters including the method of application, i.e. whether at ground level or from aircraft, the activity of the particular toxicant against the acarid and weather conditions in the area being treated.

In the preparation of dust compositions or wettable powders, the present acaricides can be blended with many commonly employed finely divided solids, such a as s earth, attapulgite, bentonite, pyrophyllite, vemriculite, diatomaceous earth, talc, chalk, gypsum, wood flour, and the like. The finely divided carrier is ground or mixed with the acaricidal toxicant or wetted with a dispersion of the toxicant in a volatile liquid. Depending upon the proportions of ingredients, these compositions can be employed as concentrates and subsequently diluted with additional solid carriers to obtain the desired amount of active toxicant. Also, such concentrate dust compositions can be incorporated in intimate admixture with surface active dispersing agents such as ionic or nonionic emulsifying or dispersing agents to form spray concentrates. Such concentrates are readily dispersible in liquid carriers to form spray compositions or liquid formulations containing the toxicants in any desired amount. The choice of surface active agent and amount employed are determined by the ability of the agent to facilitate the dispersing of the concentrate in the liquid carrier to produce the desired liquid composition. Suitable liquid carriers include water, methanol, ethanol, isopropanol, methyl ethyl ketone, acetone, methylene chloride, chlorobenzene, toluene, xylene, and petroleum distillates. Among the preferred petroleum distillates are those boiling almost entirely under 205° C. at atmospheric pressure and having a flash point above about 30° C.

Alternatively, the acaricide may be compounded with a suitable water-immiscible organic liquid and a surface active dispersing agent to produce emulsifiable concentrates which may be further diluted with water and oil to form spray mixtures in the form of oil-in-water emulsions. In such compositions, the carrier comprises an aqueous emulsion, i.e. a mixture of water-immiscible solvent, emulsifying agent and water. Preferred dispersing agents which may be employed in these compositions are oil soluble and include the condensation products of alkylene oxides with phenols and organic or inorganic acids, polyoxyethylene derivatives of sorbitan esters, alkylarylsulfonates, complex ether alcohols, mahogany soaps and the like. Suitable organic liquids to be employed in the compositions include petroleum distillates, hexanol, liquid halohydrocarbons and synthetic organic oils. The surface active dispersing agents are usually employed in the liquid dispersions and aqueous emulsions in the amount of from about 1 to about 20 percent by weight of the combined weight of the dispersing agent and the active toxicant.

The following examples demonstrate the efficacy of the present compounds as acaricides. Formulations were prepared by dissolving the compound to be tested in a mixture of acetone and a liquid alkyl-aryl polyether alcohol type surfactant (Triton X-155) and diluting the resultant composition to the desired concentration using a water-acetone mixture such that the final formulation contained 10% acetone and 10 parts per million (ppm) of the surfactant.

The activity of a given compound as a contact acaricide against the two-spotted spider mite (Tetranychus urticae) was determined by transferring adult and nymph mites to the leaves of Sieva lima bean plants. Twenty four hours following the transfer the leaves were either sprayed with or dipped into the aforementioned formulation containing 200 ppm of the compound to be tested. If the compound was to be evaluated as a systemic acaricide and ovicide 21 cc. of a formulation containing 520 ppm of the active compound was poured into the soil surrounding the infested plant.

Nine to twelve days following application of the formulation the leaves of all plants were examined using a microscope to determine the number of dead mites and eggs.

The following compounds were found to be effective contact type acaricides at a concentration of 200 ppm, in that they killed at least 70% of the adult mites, nymphs and/or eggs.

bis(p-chlorophenyl)ethylphosphine oxide
bis(p-chlorophenyl)ethylphosphine
bis(p-chloropenyl)methylphosphine oxide
bis-(p-chlorophenyl)chloromethylphosphine oxide
bis(p-chlorophenyl)propylphosphine oxide
bis(p-chlorophenyl)methylphosphine sulfide
bis(p-chlorophenyl)methylphosphine
bis(p-chlorophenyl)propylphosphine
bis(p-bromophenyl)methylphosphine oxide
bis(p-fluorophenyl)methylphosphine oxide The following compounds, which are structurally related to the present acaricides, were ineffective in controlling spider mites or their eggs (less than 30% of mites or eggs killed) at a concentration of 200 ppm.

diphenylmethylphosphine oxide
diphenylchloromethylphosphine oxide
bis(p-chlorophenyl)trichloromethylphosphine oxide
bis(m-chlorophenyl)methylphosphine oxide
tris(p-chlorophenyl)phosphine oxide
bis(p-chloro-m-nitrophenyl)methylphosphine oxide
bis(p-tolyl)methylphosphine oxide
bis(m,p-dichlorophenyl)methylphosphine oxide
bis(p-chlorophenyl)hydroxymethylphosphine oxide
bis(p-chloro-o-methylphenyl)methylphosphine oxide Two of the most effective acaricides, bis(p-chlorophenyl)methylphosphine oxide (A) and bis(p-chlorophenyl) chloromethylphosphine oxide (B) were evaluated further to ascertain the lowest concentration at which these compounds are effective. The data from this test are summarized in the following table, together with the results obtained using N'(4-chloro-o-tolyl)N,N-dimethylformamidine (Galecron), a commercially accepted miticide and ovicide. All plants were rated twelve days after being sprayed with the test formulation.

| COMPOUND | CONCENTRATION (PPM) | % CONTROL OF ADULT MITES | No. OF DEAD EGGS |
| --- | --- | --- | --- |
| A | 400 | 100 | 525 |
|   | 100 | 68 | 545 |
|   | 25 | 53 | — |
| B | 400 | 100 | 605 |
|   | 100 | 90 | 670 |
|   | 25 | 94 | — |
| Galecron (control) | 400 | 65 | 135 |
|   | 100 | 0 | — |
|   | 25 | 0 | — |

A formulation containing 100 ppm of bis(p-chlorophenyl)chloromethylphosphine oxide was poured onto the soil surrounding the roots of a Sieva lima bean plant which was infested with spider mites and eggs. Six days later 97% of the adult mites and 90% of the eggs were dead on one leaf. Examination of a second leaf revealed that 100% of the eggs had been killed.

What is claimed is:

1. A method for controlling acarids by applying to the acarids, their eggs or to substrates susceptible to infestation with said acarids an acaricidally effective amount of a phosphorus compound exhibiting the formula $$Z=P-R \quad \text{and} \quad P-R$$

(structures with benzene ring containing O and X substituents)

wherein R is selected from the group consisting of alkyl containing 1 to 12 carbon atoms, haloalkyl containing 1 to 12 carbon atoms, alkenyl containing between 2 and 12 carbon atoms and alkynyl containing between 2 and 12 carbon atoms, X represents a halogen atom selected from the group consisting of fluorine, chlorine, bromine and iodine and Z represents oxygen or sulfur.

2. The method of claim 1 wherein the phosphorus compound is present in combination with an inert liquid or inert solid diluent at a concentration of between 1 and about 500 parts per million.

3. The method of claim 1 wherein R represents an alkyl containing from 1 to 12 carbon atoms.

4. The method of claim 1 wherein R is methyl, ethyl, propyl or chloromethyl.

5. The method of claim 1 wherein X is chlorine.

6. The method of claim 1 wherein the substrate is a plant.

7. The method of claim 6 wherein the phosphorus compound is applied to the leaves of said plant.

8. The method of claim 6 wherein the phosphorus compound is applied to the soil adjacent to the roots of said plant.

* * * * *